United States Patent [19]
Wright

[11] 3,932,898
[45] Jan. 20, 1976

[54] PROSTHETIC HEART VALVE SEPARATELY FORMED CAGE

[75] Inventor: John Thomas Matthew Wright, Southport, England

[73] Assignee: National Research Development Corporation, London, England

[22] Filed: Sept. 4, 1974

[21] Appl. No.: 503,527

[30] Foreign Application Priority Data
Sept. 28, 1973 United Kingdom............... 45444/73

[52] U.S. Cl. ............ 3/1.5; 137/533.13; 137/533.15
[51] Int. Cl.² ........................................... A61F 1/22
[58] Field of Search ............ 3/1.5; 137/533, 533.11, 137/533.13, 533.15

[56] References Cited
UNITED STATES PATENTS

| | | | |
|---|---|---|---|
| 3,466,671 | 9/1969 | Siposs ..................................... | 3/1.5 |
| 3,551,913 | 1/1971 | Shiley et al. ............................ | 3/1.5 |
| 3,691,567 | 9/1972 | Cromie ................................... | 3/1.5 |
| 3,725,961 | 4/1973 | Magovern et al. ...................... | 3/1.5 |

*Primary Examiner*—Ronald L. Frinks
*Attorney, Agent, or Firm*—Cushman, Darby and Cushman

[57] ABSTRACT

The valve body of a prosthetic heart valve of annular base-cage-ball or disc type has its annular base member circumferentially grooved around its outer periphery and its cage formed with arcuate members held in such grooving. Preferably the arcuate members are formed with the other cage members from a single length of material to a closed loop configuration with four axially directed cage portions joined remotely from the base and interconnected by two diagonally opposed quadrant portions seated in the base groove. One of the base groove side walls is notched to receive the cage portions and this can provide a snap fit or the quandrants can be tied by threading in the groove.

5 Claims, 5 Drawing Figures

PROSTHETIC HEART VALVE SEPARATELY FORMED CAGE

This invention concerns fluid flow control valves and more particularly prosthetic heart valves.

The majority of currently available prosthetic heart valves can be defined as having a form comprising a valve body including an annular base member from circumferentially spaced positions of which a plurality of elongate members extend first generally axially and then mutually inwardly to define a cage, and which further comprises a movable valve member captively located in the cage for movement into and out of valve-closure seating engagement with the base member. The cage members may or may not interconnect remotely from the base member, and the movable valve member may be a ball, disc or other form.

The present invention concerns the construction of the valve body for this form of valve and, more generally, provides such a body in which the base member is grooved circumferentially around its radially outer periphery, and in which the cage members are interconnected by arcuate members held in the base member grooving.

For a clearer understanding of the invention, the same will now be more fully described, by way of example, with reference to the accompanying drawings, in which.

Figure 1:
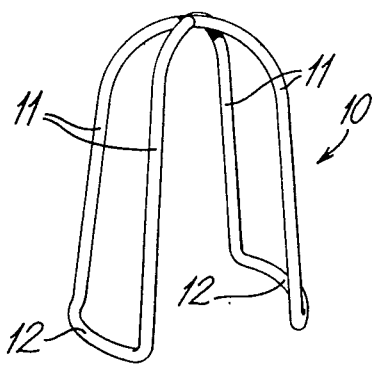
FIG. 1 illustrates the cage of one valve body according to the invention.

The cage of FIG. 1 is denoted generally at 10 and comprises four like first members 11 and two like second members 12. The first members are connected to each other at one set of corresponding ends from which they diverge in arcuate manner and then extend in rectilinear manner, the members having the collective shape of four uniformly spaced generators of a frusto-cone which is hemispherically rounded at its apex. The second members are each of arcuate shape, more specifically circular quadrant shape, and interconnect the other ends of respective pairs of the first members in a plane perpendicular to the axis of the cage.

Figure 2:
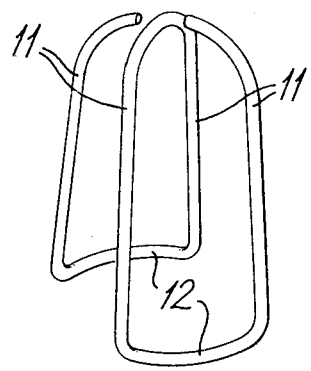
FIG. 2 illustrates the cage of FIG. 1 at an intermediate stage of construction.

This cage is advantageously made from a single length of metal which is formed to the shape of FIG. 2 and completed by welding the free ends of the terminating portions 11 to the junction of the continuously formed portions 11, i.e. at the cage apex.

Figure 3:
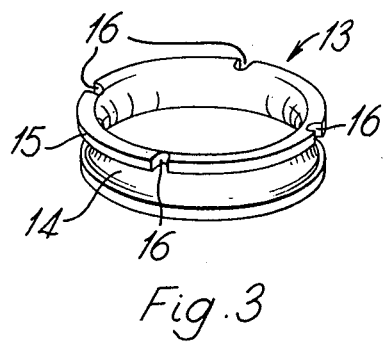
FIG. 3 illustrates a base member suitable for use with the cage of FIG. 1.

The associated base member is denoted generally at 13 in FIG. 3 and is of circular annular shape having an annular groove 14 extending circumferentially around its radially outer periphery. One side wall 15 of the groove 14 is provided with four notches 16 at uniformly spaced locations around the base member.

Figure 4:
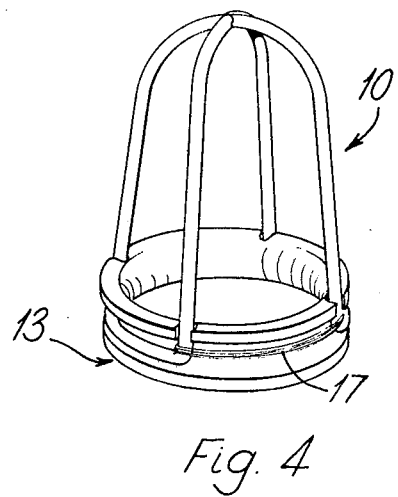
FIG. 4 illustrates the cage of FIG. 1 and the base member of FIG. 3 when assembled.

The cage 10 and base member 13 are connected as shown in FIG. 4 by locating the cage members 12 in the base member groove 14 so that the cage members 11 engage in the notches 16. The cage is then secured by passing threads 17, of which only one is shown, around the junctions of cage members 11 and 12 to span the intervening unoccupied quadrants of the groove 14, and tying these threads.

Figure 5:
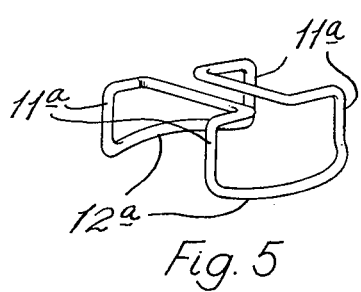
FIG. 5 illustrates another cage suitable for assembly with the base member of FIG. 3 to produce another valve body according to the invention.

It will be appreciated that, in assembly of a complete valve, a movable valve member is conveniently located in the cage before connection of the latter to the base member, and that after such connection a ring of suture material can be located in the groove 14 in accordance with existing procedures. In the present instance, the cage member is suited to use of a ball as the movable valve member, and the present preference is for use of such a valve employing rigid base and movable valve members of suitable substrate materials having a coating of pyrolytic carbon deposited thereon, and a cage of polished Stellite or titanium. However, application of the present invention is not intended to be limited in this way. For example, different cage configurations are possible and one such configuration is shown by FIG. 5 in which the first members 11a do not all interconnect remotely from the second members 12a, but are connected or integrally formed in pairs. Such a cage configuration is suited to use with a movable valve member in the form of a disc, and can be made, as with that of FIG. 1, by bending a single elongate member of metal and welding the free ends. Also, this second cage configuration is connectable with a base member of similar form to that of FIG. 3 and in similar manner to that of FIG. 4.

Also, the mode of cage and base member connection may be varied, such as by use of a snap fit of the former into the groove and/or notches of the latter; and it will, in any case, be apparent that accomodation of the cage second members in the base member does not necessitate a groove wholly circumscribing the latter.

Regarding the advantages of the invention: this arises from the fact that initial manufacture of prosthetic heart valves of the general form in question involved integration of the cage and base member, with use of a movable valve member of resilient material whereby this member could be captively located. Since then, a preference has arisen for movable valve members of rigid materials, and this has introduced complications in valve construction and assembly. The present invention reduces these complications by the provision of components which can be made and assembled in relatively simple manner to produce a secure assembly having a geometry predetermined by the components themselves.

Lastly, it is to be noted that, while the invention has been described with reference to prosthetic heart valves, such valves also find application in connection with heart by-pass and similar equipment for handling blood.

I claim:

1. In a prosthetic heart valve comprising a valve body including an annular base member, from circumferentially spaced positions of which a plurality of elongate members extend first generally axially and then mutually inwardly to define a cage, and which further comprises a movable valve member captively located in said cage for movement into and out of valve-closure seating engagement with said base member, the improved valve body construction in which:

said base member is formed with a circumferential groove around its radially outer periphery;

said elongate cage members are interconnected by arcuate members held in said groove;

said elongate cage members and said arcuate members are defined by successive portions of a single elongate member having its free ends fixed to other points therealong to form a closed loop configuration;

and said configuration includes two arcuate member portions of diametrally opposed quadrant shape and location, and four elongate cage member portions extending generally axially from respective ends of said arcuate member portions, said elongate cage member portions being formed mutually inwardly and interconnected at their ends remote from said arcuate member portions.

2. A valve according to claim 1 wherein said cage member portions have the collective shape of four uniformly spaced generators of a frusto-cone which is hemispherically rounded at its apex.

3. A valve according to claim 1 wherein each cage member portion is connected, remotely from said arcuate member portions, only with that cage member portion extending from the respectively adjacent end of the other arcuate member portion.

4. In a prosthetic heart valve comprising a valve body including an annular base member, from circumferentially spaced positions of which a plurality of elongate members extend first generally axially and then mutually inwardly to define a cage, in which further comprises a movable valve member captively located in said cage for movement into and out of valve-closure seating engagement with said base member, the improved valve body construction in which:
- said base member is formed with a circumferential groove around its radially outer periphery;
- said elongate cage members are interconnected by arcuate members located in said groove;
- one side wall of said groove is notched to receive said elongate cage members;
- and adjacent junctions of said elongate cage members and said arcuate members are tied by thread passing along said groove to hold said cage in said base member.

5. In a prosthetic heart valve comprising a valve body including an annular base member, from circumferentially spaced positions of which a plurality of elongate members extend first generally axially and then mutually inwardly to define a cage, and which further comprises a movable valve member captively located in said cage for movement into and out of valve-closure seating engagement with said member, the improved valve body construction in which:
- said base member is formed with a circumferential groove around its radially outer periphery;
- said elongate cage members are interconnected by arcuate members located in said groove;
- and one side wall of said groove is notched to receive said elongate cage members in a snap-fit to hold said cage in said base member.

* * * * *